United States Patent
Becker et al.

(10) Patent No.: US 6,913,734 B2
(45) Date of Patent: Jul. 5, 2005

(54) PROCESS AND APPARATUS FOR FLUID BED REACTIONS

(75) Inventors: Stanley John Becker, Addlestone (GB); Timothy Crispin Bristow, Beverley (GB); Robert William Clarke, Driffield (GB); Michele Fiorentino, Aix Provence (FR); David Newton, Farnham (GB); Ian All Beattie Reid, Southfields (GB); Bruce Leo Williams, Brough (GB)

(73) Assignee: BP Chemicals Limited, London (GB)

( * ) Notice: Subject to any disclaimer, the term of this patent is extended or adjusted under 35 U.S.C. 154(b) by 687 days.

(21) Appl. No.: 09/877,227

(22) Filed: Jun. 11, 2001

(65) Prior Publication Data

US 2002/0016374 A1 Feb. 7, 2002

(30) Foreign Application Priority Data

Jun. 14, 2000 (GB) .............................. 0014584

(51) Int. Cl.⁷ ................................. B01J 8/08
(52) U.S. Cl. ....................................... 422/139
(58) Field of Search .................. 518/700; 422/139, 422/140, 143

(56) References Cited

U.S. PATENT DOCUMENTS 3,615,253 A * 10/1971 Warzel ........................ 422/131
4,579,999 A    4/1986  Gould et al.
5,541,270 A    7/1996  Chinh et al.
5,866,737 A    2/1999  Hagemeyer et al.

FOREIGN PATENT DOCUMENTS

| EP | 0 546 677 A1 | 6/1993 |
| EP | 0 685 449 A1 | 12/1995 |
| EP | 0 785 177 A2 | 7/1997 |
| EP | 0 847 982 | 6/1998 |
| EP | 0 985 655 | 3/2000 |
| EP | 1 006 100 A | 6/2000 |
| EP | 1 043 064 A2 | 10/2000 |
| GB | 1 265 770 A | 3/1972 |
| WO | 99/51339 | 10/1999 |

* cited by examiner

Primary Examiner—Jonathan Johnson
(74) Attorney, Agent, or Firm—Nixon & Vanderhye

(57) ABSTRACT

A process and apparatus for contacting (a) at least one gaseous reactant and (b) at least one liquid selected from the group consisting of reactants, coolants and mixtures thereof in the presence of a fluidized bed of catalyst, in which the liquid is introduced into the reactor through at least one inlet located within the fluidization zone and the gaseous reactant is introduced into the reactor through at least one inlet located within the fluidization zone adjacent the support means.

13 Claims, 1 Drawing Sheet

PROCESS AND APPARATUS FOR FLUID BED REACTIONS

The present invention relates in general to fluid bed heterogeneous gas-phase reactions and to apparatus for same.

BACKGROUND OF THE INVENTION

Fluid bed reactors and their use in processes involving a molecular oxygen-containing gas with a solid catalyst for a heterogeneous gas phase reaction are known, for example from EP-A-0546677, EP-A-0685449 and EP-A-0847982.

EP-A-0546677 discloses a process for oxidising ethane to acetic acid in a fluidized bed reaction zone. In the example illustrated in EP-A-0546677, ethane is joined with a recycle stream containing water, CO, $CO_2$, $O_2$, ethylene and ethane and the combined stream is fed to the fluid bed reactor. A molecular oxygen-containing stream and steam are introduced separately into the fluid bed reactor. The hot oxidation products exit the top of the reactor.

EP-A-0685449 discloses a process for manufacturing vinyl acetate in a fluid bed reactor comprising feeding ethylene and acetic acid into the fluid bed reactor through one or more inlets, feeding an oxygen-containing gas into the fluid bed reactor through at least one further inlet, co-joining the oxygen-containing gas, ethylene and acetic acid in the fluid bed reactor while in contact with a fluid bed catalyst material to enable the ethylene, acetic acid and oxygen to react to produce vinyl acetate and recovering the vinyl acetate from the fluid bed reactor. According to EP-A-0685449, the oxygen may be added in pure form or as an admixture with inert gas such as nitrogen or carbon dioxide. Since the oxygen and hydrocarbons are not mixed until they are both inside the reactor, catalyst is present when they meet and reaction proceeds immediately, causing the oxygen partial pressure to drop. Thus, an advantage of feeding an oxygen-containing gas to the reactor through at least one further inlet in addition to the ethylene and acetic acid reactants is that it allows significantly higher levels of oxygen to be safely employed without a high inventory of flammable gas mixtures.

EP-A-0847982 discloses a process for the production of vinyl acetate by reacting at elevated temperature in a fluid bed reactor ethylene, acetic acid and an oxygen-containing gas in the presence of a fluid bed catalyst material characterised in that a liquid is introduced into the fluidised reactor for the purpose of removing heat therefrom by evaporation of the liquid. According to EP-A-0847982, the liquid introduced into the fluidised bed reactor may suitably be a reactant, an inert liquid or a product of the reaction, or a mixture of any two or more thereof. Thus, at least a part of the acetic acid reactant may be fed to the fluidised bed reactor in liquid form. A suitable product is said to be water, which is formed as a by-product of the reaction of ethylene, acetic acid and oxygen, because it has a relatively high latent heat of evaporation. It is stated therein that vinyl acetate product and/or acetaldehyde by-product may also be recycled and introduced in liquid form into the fluidised bed reactor.

According to EP-A-0847982, the liquid may be introduced into the fluidised-bed reactor by suitably arranged injection means. It is stated that a single injection means may be used or a plurality of injection means may be arranged within the fluidised bed reactor. According to EP-A-0847982, for introducing liquid into the fluidised catalyst bed, the number of injection means used is that number which is required to provide sufficient penetration and dispersion of liquid at each injection means to achieve good dispersion of liquid across the fluidised catalyst bed. A preferred injection means is said to be a nozzle or a plurality of nozzles which include gas-induced atomising nozzles in which a gas is used to assist in the injection of the liquid, or liquid-only spray-type nozzles. According to EP-A-0847982, liquid may be introduced with the ethylene and/or oxygen-containing gas and/or recycle gas fed to the fluidised bed reactor suitably by bubbling the ethylene and/or oxygen-containing gas and/or recycle gas through the liquid prior to its introduction into the reactor. In a further alternative, it is stated that liquid may be pumped into the area of the grid plate forming an essential component of a fluid bed reactor where contact with incoming ethylene and/or oxygen-containing gas and/or recycle gas would propel the liquid upwards into the fluidised catalyst bed. In yet a further alternative, it is stated that liquid may be pumped into the reactor via a sparge bar or bars, optionally with one or more of the gaseous feeds.

According to EP-A-0847982, the nozzle or nozzles may be located in the reactor grid or in the reactor walls above the grid.

EP-A-0985655 discloses a fluid bed process for the production of vinyl acetate which comprises feeding ethylene, liquid acetic acid and an oxygen-containing gas into a fluid bed reactor in which the amount of co-promoter is up to 6% by weight of the catalyst. It is stated therein that the acetic acid is introduced into the reactor in liquid form, optionally with some acid in the vapour form and that the liquid acetic acid may be introduced into the fluid bed reactor by any suitable injection means, for example a nozzle which may be a gas-induced atomising nozzle or liquid-only spray-type nozzles. It is also stated therein that one or more nozzles may be used and that additionally, recycled acetic acid may be introduced into the reactor either pre-mixed with the crude acetic acid or using a separate injection means In the examples illustrated in EP-A-0985655, fresh acetic acid from storage (1) and recycle acetic acid are pumped together with some recycle gas (3) to twin fluid nozzle within the fluid bed (2). The remainder of the recycle gas feed (3), fresh ethylene (4) and oxygen (5) enter the plenum and through a sintered plate into the reactor. Fresh oxygen (6) may be fed directly into the fluid bed. A freeboard section is provided for disengaging the catalyst (7). The gaseous products exit the reactor through exit (8) through sintered filter elements (not shown).

There is a need for an improved process and apparatus for fluid bed heterogeneous gas-phase reactions in which at least one gas and at least one liquid are introduced to a fluidised bed of catalyst.

SUMMARY OF THE INVENTION

Thus, according to one embodiment of the present invention there is provided a process for contacting (a) at least one gaseous reactant and (b) at least one liquid selected from the group consisting of reactants, coolants and mixtures thereof in the presence of a fluidised bed of catalyst, which process comprises:

(i) fluidising with a fluidising gas, a bed of fluidisable catalyst within a fluidisation zone in a reactor, said reactor having a fluidisation zone for said bed of catalyst and means for supporting said bed of catalyst within said fluidisation zone;

(ii) introducing said at least one liquid into said reactor through at least one inlet located within said fluidisation zone; and (iii) introducing said at least one gaseous reactant into said reactor through at least one inlet located within said fluidisation zone adjacent said support means.

According to another embodiment of the present invention there is provided apparatus for fluid bed heterogeneous reactions in which (a) at least one gaseous reactant and (b) at least one liquid selected from the group consisting of reactants, coolants and mixtures thereof, are introduced into a fluidised bed of catalyst, which apparatus comprises a reactor having:
(1) a fluidisation zone for a fluidised bed of catalyst;
(2) means for supporting a fluidised bed of catalyst within said fluidisation zone;
(3) at least one inlet for introducing at least one gaseous reactant into said reactor; and
(4) at least one inlet for introducing at least one liquid selected from the group
consisting of reactants, coolants and mixtures thereof into said reactor, in which said at least one inlet for liquid is located within said fluidisation zone and said at least one inlet for gaseous reactant is located within said fluidisation zone adjacent said support means.

In the process and apparatus of the present invention, the liquid reactant and/or coolant introduced into the fluidised bed of catalyst may be introduced at any position relative to the support within the fluidisation zone because the recirculation of the fluidised catalyst distributes it throughout the zone. An advantage of the liquid being distributed by the fluidised catalyst is that fewer inlets for liquid may be required. The distribution of the liquid by the fluidised catalyst may be facilitated by a suitable porosity of the catalyst and/or by use of suitable chemical reagents.

In the process and apparatus of the present invention, introducing the gaseous reactant into the fluidised bed of catalyst through at least one inlet located within said fluidisation zone adjacent said support means provides a long contact time between the gaseous reactant and the fluidised bed of catalyst and also provides a high concentration of the gaseous reactant through-out the bed. This is beneficial for reactions where the rate of reaction is dependent upon the concentration of the gaseous reactant, such as oxygen in the acetoxylation of ethylene to produce vinyl acetate. Whilst introducing the gaseous reactant into a plenum below the catalyst bed support might also provide a long contact time between the gaseous reactant and the catalyst, this may be restricted. For example, if the gaseous reactant comprises molecular oxygen, there is a need to avoid potentially explosive mixtures and/or large inventories of molecular oxygen-containing gas within the reactor.

Suitable fluid bed processes for use in the present invention include the acetoxylation of olefins, for example the reaction of ethylene, acetic acid and oxygen to produce vinyl acetate as described in EP-A-0847982, the contents of which are hereby incorporated by reference. In this process the gaseous reactant comprises a molecular oxygen-containing gas which may be introduced to the reactor together with the ethylene or preferably at least in pale separately from the ethylene. The fluidising gas may comprise ethylene and oxygen as flesh feed and as components of recycled gas. At least part of the acetic acid reactant is introduced as liquid reactant and/or coolant. Other liquids may be introduced as coolants. By introducing a molecular oxygen containing gas through at least one inlet located within the fluidisation zone adjacent the fluid bed support means, a long contact time of the oxygen with the catalyst is obtained without risking explosive mixtures within a plenum of the reactor. Liquid acetic acid reactant and coolant introduced into fluidised bed of catalyst in the reactor through at least one inlet located within the fluidisation zone is absorbed by the catalyst and distributed around the reactor by the fluidised bed of catalyst. Therefore, the liquid inlet(s) need not be located at the base of the fluidisation zone. The acetic acid may be replaced in part by acetic anhydride.

Another suitable process for use in the present invention is the oxidation of ethylene to acetic acid and/or the oxidation of ethane to ethylene and/or acetic acid in which a liquid selected from acetic acid, water and mixtures thereof are introduced into the reactor.

Yet another suitable process for use in the present invention is the production of acrylonitrile by the reaction of propylene, propane or mixtures thereof with ammonia and oxygen-containing gas in which heat of reaction is removed at least in part by the introduction of liquid (reactant, coolant or mixtures thereof).

Another suitable process for use in the present invention is the production of maleic anhydride from butene, butane or mixtures thereof.

More than one inlet for gaseous reactant may be used in the present invention. The gaseous reactant for these inlets may be provided from a common source such as a common end box. Gaseous reactant and other gases may be introduced additionally to the reactor by other inlets, for example as components in recycle gases and/or mixed feed gases. Gaseous reactant and other gases may be introduced as a component of the fluidising gas, to the reactor through a plenum below the catalyst support means.

Suitably, the gaseous reactant may comprise a molecular oxygen-containing gas. Suitable molecular oxygen-containing gases for use in the present invention include oxygen gas with minor amounts of impurities such as argon and nitrogen which each may be present at a concentration of less than 0.1% by volume. The concentration of oxygen in the molecular oxygen-containing gas is suitably in the range 10 to 100%, preferably in the range 50 to 100%, for example a concentration of greater than 99.5% by volume, suitably a concentration of at least 99.6% by volume.

Any suitable inlet for the gaseous reactant may be used in the present invention, in particular recognising the hazards which may have to be considered with such reactants. Thus, for example, if the gaseous reactant introduced adjacent the catalyst support means comprises a molecular oxygen-containing gas, for safety, it is preferably located at a distance from the catalyst support means of greater than any potential flame length. The potential flame length is determined by factors such as the inlet pipe diameter and inlet gas velocity. The inlets should be positioned and inlet pressures and velocities selected, so that the molecular oxygen-containing gas is dispersed and mixed in the region of the inlet. The inlets should be positioned not too close to the reactor walls, in case there is a shock wave following a detonation. The inlets should be positioned so that the molecular oxygen-containing gas does not impinge directly on surface or other structures in the reactor such as inlets for other reactants.

The liquid introduced into the reactor may be introduced into the fluidised bed of catalyst for the purpose of removing heat therefrom by evaporation of the liquid, as a reactant or as a combination of these purposes. Introducing liquid into the fluidised bed of catalyst has that advantage of introducing it where heat is produced in exothermic reactions. Thus, the liquid introduced into the fluidised bed of catalyst may suitably be a reactant, an inert liquid or a product of the reaction, or a mixture of any two or more thereof. In the acetoxylation of ethylene with a molecular oxygen containing gas and acetic acid, for example, the acetic acid reactant may be fed to the fluidised bed of catalyst in liquid form; a suitable product which may be introduced into the fluidised bed of catalyst is water, which is formed for example, as a by-product of the acetoxylation reaction and has a relatively high latent heat of evaporation; and vinyl acetate product and/or acetaldehyde by-product may also be recycled and introduced in liquid form into the fluidised bed of catalyst in a process for production of vinyl acetate.

Preferably, the inlet for the liquid is located in the lower half of the fluidisation zone, thereby increasing the opportunity for the liquid to be distributed by the catalyst. Preferably, the inlet for the liquid is positioned such that the liquid does not impinge on any solid surfaces within the fluidisation zone, such as the surface of cooling coils located within the fluidisation zone to remove heat of reaction. Since the liquid introduced into the reaction zone may have a significant momentum, it may assist is creating and/or stabilising circulation within the fluidised bed.

Additionally, one or more second gaseous reactants may also be introduced into the reactor together with or preferably at least in part, separately from the gaseous reactant such as molecular oxygen containing gas. This second gaseous reactant may be introduced as a component of the fluidising gas. The fluidising gas may comprise fresh gaseous reactants and/or recycle gases. The second gaseous reactant introduced into the reactor may be, for example (i) ethylene and/or (ii) ethane which may be reacted with the molecular oxygen-containing gas to produce respectively (i) acetic acid and/or (ii) ethylene and/or acetic acid. Ethylene may also be used with molecular oxygen-containing gas and acetic acid to produce vinyl acetate. Ethylene and/or ethane in these reactions may be used in substantially pure form or admixed with one or more of nitrogen, methane, ethane, carbon dioxide and water in the form of steam or one or more of hydrogen, $C_3/C_4$ alkenes or alkanes.

If oxygen-containing gas is mixed with other gaseous reactants (as fresh feed and/or as recycle gas) outside of the reactor, the resultant mixture should have a composition outside the flammability region.

The process of the present invention may suitably be operated at a temperature from 100 to 500° C., preferably 140 to 400° C. The process may suitably be operated at a pressure of 10 to 3000 kPa gauge (0.1 to 30 barg), preferably 20 to 2500 Pa gauge (0.2 to 25 barg).

In the fluidisation zone of the reactor, the particles of the catalyst are maintained in a fluidized state by suitable gas flow through the bed of catalyst.

The catalyst may be any suitable fluidisable catalyst. The catalyst may be a supported catalyst. Suitable catalyst supports include porous silica, alumina, silica/alumina, titania, silica/titania, zirconia and mixtures thereof. Preferably, the support is silica. Suitably, the support may have a pore volume from 0.2 to 3.5 mL per gram of support, a surface area of 5 to 800 m² per gram of support and an apparent bulk density of 0.3 to 5.0 g.mL.

A typical catalyst composition useful in this invention, may have the following particle size distribution

| | |
|---|---|
| 0 to 20 microns | 0–30 wt % |
| 20 to 44 microns | 0–60 wt % |
| 44 to 88 microns | 10–80 wt % |
| 88 to 106 microns | 0–80 wt % |
| >106 microns | 0–40 wt % |
| >300 microns | 0–5 wt % |

Persons skilled in the art will recognise that support particles sizes of 44, 48, 106 and 300 microns are arbitrary measures in that they are based on standard sieve sizes. Particle sizes and particle size distributions may be measured by an automated laser device such as a Microtrac X100

Suitably, the catalyst has a bulk density of from 0.5 to 5 g/cm³, preferably 0.5 to 3 g/cm³, especially 0.5 to 2 g/cm³

Suitable catalysts for use in the present invention include oxidation, ammoxidation and acetoxylation catalysts A catalyst suitable for use in the production of vinyl acetate by the acetoxylation of ethylene may comprise a Group VIII metal, a catalyst promoter and an optional co-promoter. The catalyst may be prepared by any suitable method, such as that described in EP-A-0672453. The Group VIII metal is preferably palladium. The Group VIII metal may be present in a concentration of greater than 0.2% by weight, preferably greater than 0.5% by weight based upon total weight of catalyst. The metal concentration may be as high as 10% by weight. Suitable promoters include gold, copper, cerium or mixtures thereof. A preferred promoter is gold. The promoter metal may be present in an amount of from 0.1 to 10% by weight in the finished catalyst. Suitable co-promoters include Group I, Group II, lanthanide or transition metals, for example selected from the group consisting of cadmium, barium, potassium, sodium, manganese, antimony, lanthanum and mixtures thereof, which are present in the finished catalyst as salts, e.g. an acetate salt. The preferred salts are potassium or sodium acetate. The co-promoter is preferably present in the catalyst composition in a concentration of 0.1 to 15% by weight of catalyst, more preferably, from 1 to 5% by weight. When a liquid acetic acid feed is used, the preferred concentration of co-promoter salt is up to 6% by weight, especially 2.5% to 5.5%. Where the acid is introduced in the vapour phase the co-promoter salt is preferably present in a concentration up to 11 wt %.

Catalyst suitable for the oxidation of ethane to ethylene and/or acetic acid and/or for the oxidation of ethylene to acetic acid are described in EP-A-1043064 and WO 99/51339, the contents of which are hereby incorporated by reference.

BRIEF DESCRIPTION OF THE DRAWING

The invention will now be illustrated by way of example only and with reference to the drawings in which.

DETAILED DESCRIPTION OF PREFERRED EMBODIMENTS

Figure 1:
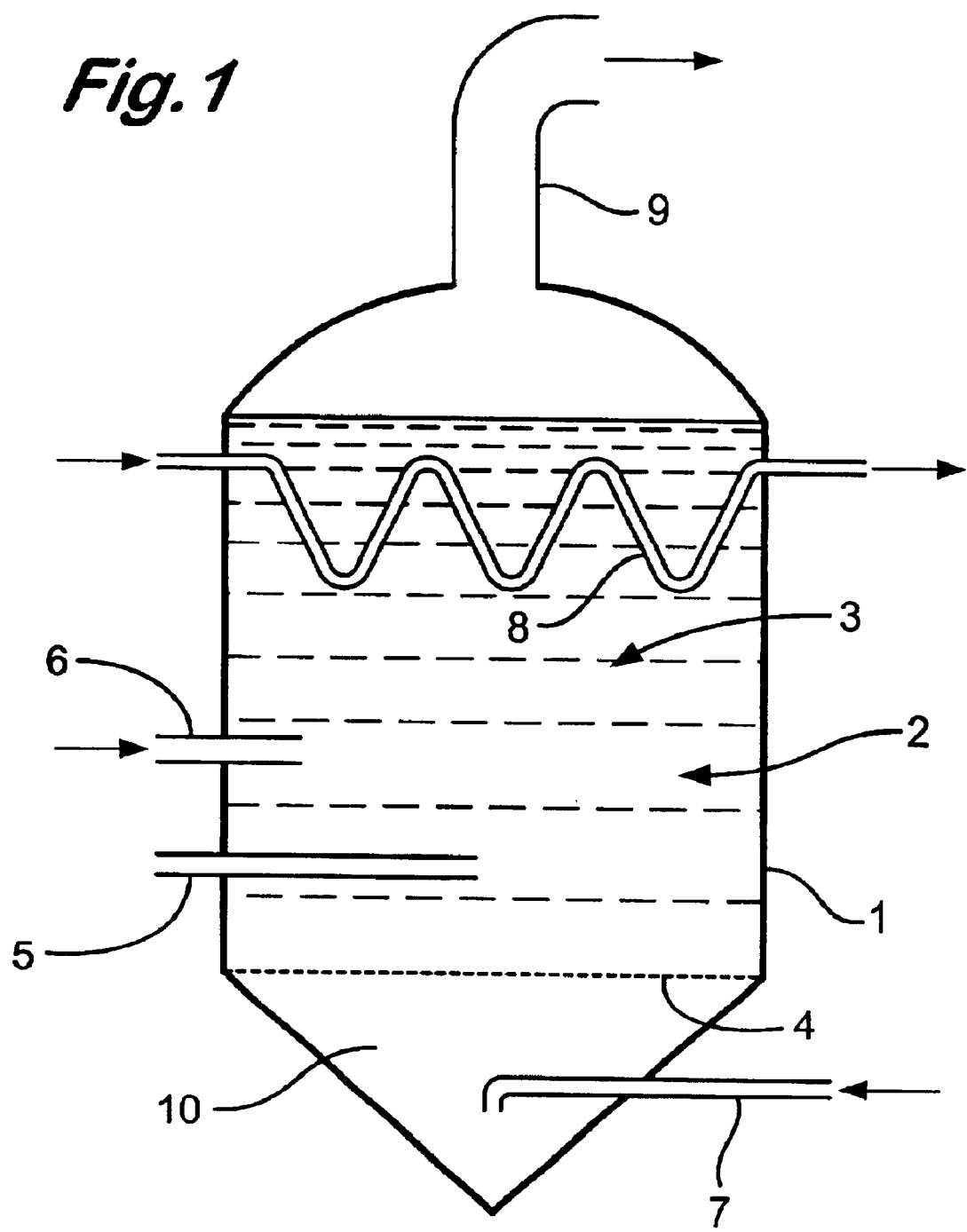
FIG. 1 represents in schematic form, a longitudinal cross-section of a fluid bed reactor according to the present invention.

Referring to FIG. 1. A reactor (1) for a fluid bed reaction such as the acetoxylation of ethylene to vinyl acetate contains in use, a fluidized bed of fluidisable catalyst (2), for example a palladium/gold catalyst supported on a silica support. The fluidised bed of catalyst is supported in a fluidisation zone (3) in the reactor (1) by a suitable support grid (4). The reactor (1) is provided with at least one inlet pipe (5) for a molecular oxygen-containing gas which inlet is located within the fluidisation zone (3) adjacent the support grid (4). The reactor (1) is also provided with at least one inlet (6) for liquid acetic acid, which inlet is located within the fluidisation zone. The fluid bed reactor (1) is also provided with cooling coils (8) and a supply of fluidising gas comprising recycle gases, ethylene reactant and optionally oxygen reactant through inlet (7) located in plenum (10) below the support grid (4). The reactor is provided with an outlet (9). Cooling coils (8) may be used to heat the catalyst bed at start-up, being provided with a source of hot fluid.

The apparatus of FIG. 1 may be used in the acetoxylation of ethylene to produce vinyl acetate. In use, ethylene reactant and recycle gases are passed through inlet (7) to plenum (10) and thence through support grid (4) fluidise the catalyst bed (2) in the fluidisation zone (3) of the reactor (1). Liquid acetic acid reactant, is introduced into the fluidised bed (2) in the fluidisation zone (3) through inlet (6). A molecular oxygen-containing gas is introduced into the fluidised catalyst bed (2) in the fluidisation zone (3) through at least one inlet pipe (5) in the fluidisation zone adjacent the support grid (4). Heat of reaction is removed at least in part by the cooling coils (8) provided with a supply of cooling water and in part by evaporation of the liquid acetic acid. The gaseous reaction products are removed from outlet (9).

In the apparatus and process of the present invention, the liquid acetic acid introduced into the fluidisation zone is distributed throughout the zone by the recirculation of the fluidised catalyst. It may therefore be introduced relatively high up the fluidised bed of catalyst. The molecular oxygen-containing gas introduced into the fluidised bed of catalyst through the at least one inlet located within the fluidisation zone adjacent the fluidised bed support has a long contact time with the fluidised bed of catalyst.

Similar apparatus may be used for other reactions involving the use of molecular oxygen-containing gas—for example the oxidation of ethylene to acetic acid and/or the oxidation of ethane to ethylene and/or acetic acid, the ammoxidation of propylene, propane or mixtures thereof to produce acrylonitrile and the oxidation of C4's to maleic anhydride.

We claim:

1. A process for contacting (a) at least one gaseous reactant and (b) at least one liquid selected from the group consisting of reactants, coolants and mixtures thereof in the presence of a fluidised bed of catalyst, which process comprises:
    (i) fluidising with a fluidising gas, a bed of fluidisable catalyst within a fluidisation zone in a reactor, said reactor having a fluidisation zone for said bed of catalyst and support means for supporting said bed of catalyst within said fluidisation zone;
    (ii) introducing said at least one liquid into said reactor through at least one inlet located within said fluidisation zone; and
    (iii) introducing said at least one gaseous reactant into said reactor through at least one inlet located within said fluidisation zone adjacent said support means.
2. A process as claimed in claim 1 in which said at least one inlet for liquid is located in the lower half of the fluidisation zone.
3. A process as claimed in claim 1 in which said at least one inlet for liquid is located so that liquid does not impinge on any solid surfaces within the fluidisation zone.
4. A process as claimed in claim 1 in which said gaseous reactant comprises molecular oxygen containing gas.
5. A process as claimed in claim 4 in which said at least one inlet for gaseous reactant is located at a distance from said catalyst support means of greater than any potential flame length.
6. A process as claimed in claim 4 in which one or more second gaseous reactants are introduced into the reactor.
7. A process as claimed in claim 6 in which said one or more second reactants are introduced at least in part, separately from said first gaseous reactant.
8. A process as claimed in claim 6 in which said one or more second gaseous reactants are introduced as a component of the fluidising gas.
9. A process as claimed in claim 6 in which said one or more second gaseous reactants comprises ethane, ethylene or mixtures thereof.
10. A process as claimed in claim 9 in which said liquid introduced into said reactor comprises acetic acid and there is produced vinyl acetate.
11. A process as claimed in claim 9 in which said liquid introduced into said reactor is selected from the group consisting of acetic acid, water and mixtures thereof and there is produced acetic acid by the oxidation of ethylene and/or there is produced ethylene and/or acetic acid by the oxidation of ethane.
12. A process as claimed in claim 6 in which acrylonitrile is produced by the reaction of ammonia, molecular oxygen-containing gas and a second reactant selected from the group consisting of propylene, propane and mixtures thereof.
13. A process as claimed in claim 6 in which maleic anhydride is produced by the reaction of molecular oxygen-containing gas and a second reactant selected from the group consisting of butane, butane and mixtures thereof.

* * * * *